(12) United States Patent
Shturman

(10) Patent No.: US 8,137,369 B2
(45) Date of Patent: Mar. 20, 2012

(54) ROTATIONAL ATHERECTOMY DEVICE WITH FLUID INFLATABLE SUPPORT ELEMENTS SUPPORTED BY FLUID BEARINGS

(75) Inventor: Leonid Shturman, Nyon (CH)

(73) Assignee: Lela Nadirashvili, Nyon (CH)

( * ) Notice: Subject to any disclaimer, the term of this patent is extended or adjusted under 35 U.S.C. 154(b) by 0 days.

(21) Appl. No.: 12/373,418

(22) PCT Filed: Jun. 28, 2007

(86) PCT No.: PCT/EP2007/056500
§ 371 (c)(1),
(2), (4) Date: Jan. 12, 2009

(87) PCT Pub. No.: WO2008/006705
PCT Pub. Date: Jan. 17, 2008

(65) Prior Publication Data
US 2009/0326568 A1    Dec. 31, 2009

(30) Foreign Application Priority Data
Jul. 13, 2006 (GB) .................................. 0613980.2

(51) Int. Cl.
*A61B 17/22* (2006.01)
(52) U.S. Cl. ..................................................... 606/159
(58) Field of Classification Search .................. 606/110, 606/113, 114, 127, 128, 170, 180, 191, 159; 604/22, 103.01, 103.02, 154, 155, 35
See application file for complete search history.

(56) References Cited

U.S. PATENT DOCUMENTS

| 1,431,416 A | 10/1922 | Parsons et al. |
| 1,916,085 A | 6/1933 | Summers et al. |
| 4,646,736 A | 3/1987 | Auth |
| 4,870,953 A | 10/1989 | DonMicheal et al. |

(Continued)

FOREIGN PATENT DOCUMENTS
EP        0419154        3/1991
(Continued)

OTHER PUBLICATIONS

International Search Report, WO 2008/006705 A3 (published Apr. 10, 2008), corresponding to Int'l Application No. PCT/EP2007/056500.

(Continued)

*Primary Examiner* — Ryan Severson
*Assistant Examiner* — David Eastwood
(74) *Attorney, Agent, or Firm* — Fish & Richardson P.C.

(57) ABSTRACT

A rotational atherectomy device for removing a stenotic tissue from a vessel of a patient is disclosed. The device comprises a rotatable, flexible, hollow drive shaft having an open distal end. The drive shaft comprising a fluid impermeable wall, an abrasive element mounted to the drive shaft proximal to and spaced away from its distal end, the fluid impermeable wall being formed from a torque transmitting coil and at least one fluid impermeable membrane which define a lumen for the antegrade flow of pressurized fluid through the drive shaft and into a distal fluid inflatable support element to inflate said fluid inflatable support element. The distal fluid inflatable support element is located at the distal end of the drive shaft and has an outer wall comprising an outflow opening located such that said outflow opening faces an inner surface of a treated vessel during rotation of the drive shaft so that a flow of fluid out of said opening forms a layer of fluid between the outer wall of the fluid inflatable distal support element and a wall of the treated vessel. The layer of fluid forming a fluid bearing between the outer wall of the rotating fluid inflated distal support element and the wall of the treated vessel.

16 Claims, 11 Drawing Sheets

U.S. PATENT DOCUMENTS

| | | | |
|---|---|---|---|
| 4,931,635 A | 6/1990 | Toyama | |
| 4,990,134 A | 2/1991 | Auth | |
| 5,100,425 A | 3/1992 | Fischell et al. | |
| 5,217,474 A | 6/1993 | Zacca et al. | |
| 5,242,460 A * | 9/1993 | Klein et al. | 606/159 |
| 5,250,060 A * | 10/1993 | Carbo et al. | 606/159 |
| 5,273,526 A | 12/1993 | Dance | |
| 5,308,354 A | 5/1994 | Zacca et al. | |
| 5,314,438 A | 5/1994 | Shturman | |
| 5,342,292 A | 8/1994 | Nita et al. | |
| 5,361,285 A | 11/1994 | Formanek et al. | |
| 5,370,653 A | 12/1994 | Cragg | |
| 5,458,575 A | 10/1995 | Wang | |
| 5,584,843 A | 12/1996 | Wulfman et al. | |
| 5,681,336 A * | 10/1997 | Clement et al. | 606/159 |
| 5,843,103 A * | 12/1998 | Wulfman | 606/159 |
| 5,868,708 A * | 2/1999 | Hart et al. | 604/104 |
| 6,010,533 A | 1/2000 | Pope et al. | |
| 6,096,054 A | 8/2000 | Wyzgala et al. | |
| 6,132,444 A | 10/2000 | Shturman et al. | |
| 6,135,982 A | 10/2000 | Campbell | |
| 6,146,395 A | 11/2000 | Kanz et al. | |
| 6,152,911 A | 11/2000 | Giannoble | |
| 6,156,048 A | 12/2000 | Wulfman et al. | |
| 6,241,706 B1 | 6/2001 | Leschinsky et al. | |
| 6,270,465 B1 | 8/2001 | Keith et al. | |
| 6,416,526 B1 | 7/2002 | Wyzgala et al. | |
| 6,485,500 B1 * | 11/2002 | Kokish et al. | 606/194 |
| 6,491,660 B2 | 12/2002 | Guo et al. | |
| 6,685,718 B1 | 2/2004 | Wyzgala et al. | |
| 6,955,661 B1 | 10/2005 | Herweck et al. | |
| 2002/0007190 A1 * | 1/2002 | Wulfman et al. | 606/167 |
| 2002/0082547 A1 * | 6/2002 | Deniega et al. | 604/48 |
| 2002/0099367 A1 * | 7/2002 | Guo et al. | 606/43 |
| 2002/0138088 A1 | 9/2002 | Nash et al. | |
| 2002/0188276 A1 | 12/2002 | Evans et al. | |
| 2003/0199889 A1 | 10/2003 | Kanz et al. | |
| 2004/0098014 A1 | 5/2004 | Flugelman et al. | |
| 2004/0158270 A1 | 8/2004 | Wyzgala et al. | |
| 2005/0154416 A1 | 7/2005 | Herweck et al. | |
| 2005/0209615 A1 | 9/2005 | Prudnikov et al. | |
| 2005/0240146 A1 * | 10/2005 | Nash et al. | 604/35 |
| 2005/0256461 A1 * | 11/2005 | DiFiore et al. | 604/247 |

FOREIGN PATENT DOCUMENTS

| | | |
|---|---|---|
| WO | WO 9850101 A1 | 11/1998 |
| WO | WO99/44513 | 9/1999 |
| WO | WO 02/09599 | 2/2002 |
| WO | WO2006/126175 | 11/2006 |
| WO | WO 2006/126176 | 11/2006 |
| WO | WO 2006126076 A2 | 11/2006 |

OTHER PUBLICATIONS

Declaration of Aleksey Filippov, Apr. 23, 2007, 1 page.

Declaration of Dmitri Prudnikov, Apr. 23, 2007, 1 page.

Excerpt from Deposition of Dmitri Prudnikov, Mar. 5, 2008, 7 pages.

Excerpt from Deposition of Dmitri Prudnikov, Mar. 6, 2008, 54 pages.

Exhibits Nos. 14, 31 & 32, from Deposition of Dmitri Prudnikov, Mar. 5, 2008, 3 pages.

Exhibits Nos. 33-39 from Deposition of Dmitri Prudnikov, Mar. 6, 2008, 47 pages.

* cited by examiner

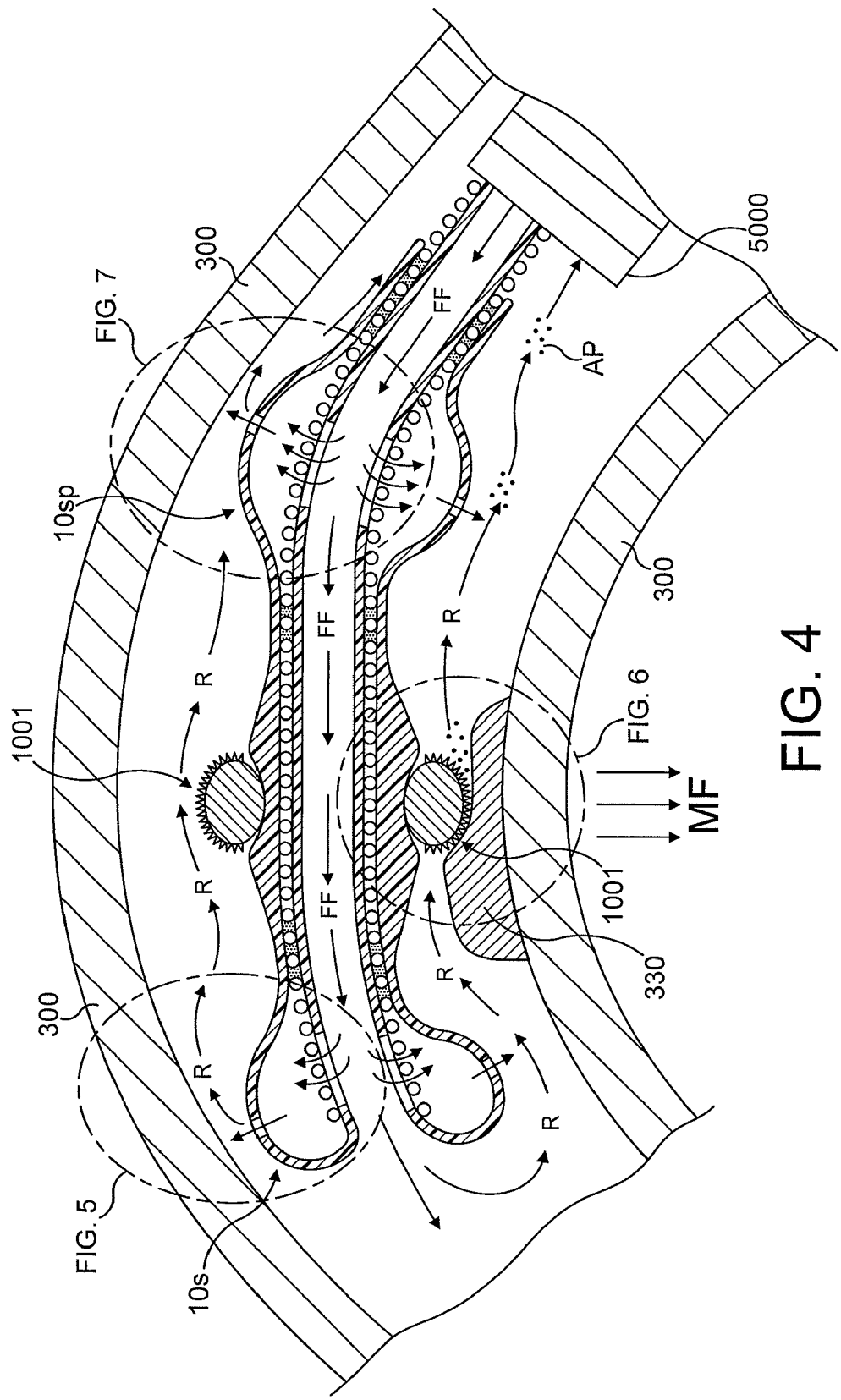

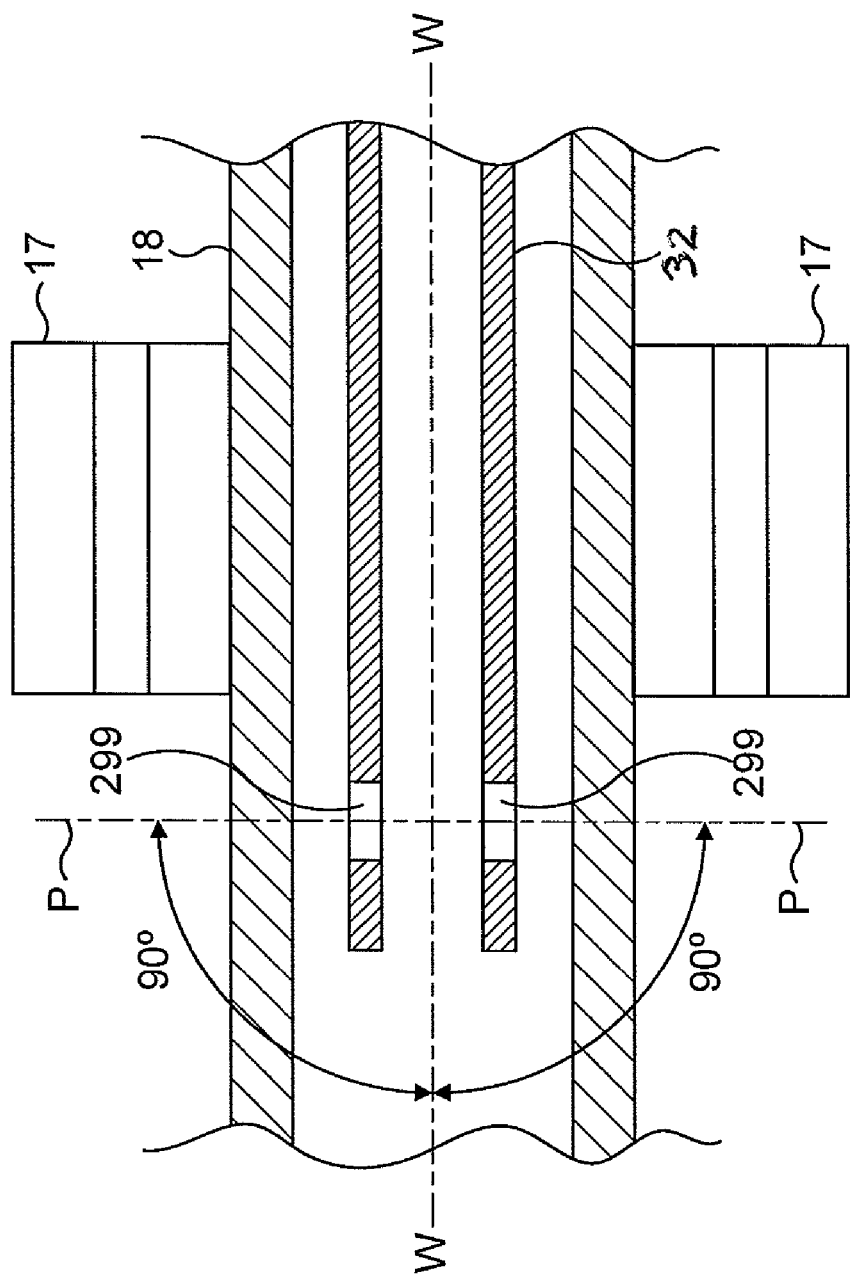

ROTATIONAL ATHERECTOMY DEVICE WITH FLUID INFLATABLE SUPPORT ELEMENTS SUPPORTED BY FLUID BEARINGS

CROSS-REFERENCE TO RELATED APPLICATIONS

This application is a national phase application based on PCT/EP2007/056500, filed Jun. 28, 2007, the content of which is incorporated herein by reference, and claims priority of GB Patent Application No. 0613980.2, filed Jul. 13, 2006, the content of which is incorporated by herein by reference.

BACKGROUND OF THE INVENTION

1. Field

The present invention provides a rotational atherectomy device for removing a stenotic lesion from within a vessel of a patient. More specifically, the invention relates to a rotational atherectomy device for removing or reducing stenotic lesions in blood vessels such as a human artery by rotating an abrasive element within the vessel to partially or completely ablate the unwanted material.

2. Description of the Related Art

Atherosclerosis, the clogging of arteries, is a leading cause of coronary heart disease. Blood flow through the peripheral arteries (e.g., carotid, femoral, renal, etc.), is similarly affected by the development of atherosclerotic blockages. A conventional method of removing or reducing blockages in blood vessels is known as rotational atherectomy. A long guidewire is advanced into the diseased blood vessel and across the stenotic lesion. A hollow drive shaft is then advanced over the guidewire. The distal end of the drive shaft terminates in a burr provided with an abrasive surface formed from diamond grit or diamond particles. The burr is positioned against the occlusion and the drive shaft rotated at extremely high speeds (e.g., 20,000-160,000 rpm). As the burr rotates, the physician slowly advances it so that the abrasive surface of the burr scrapes against the occluding tissue and disintegrates it, reducing the occlusion and improving the blood flow through the vessel. Such a method and a device for performing the method are described in, for example, U.S. Pat. No. 4,990,134 to Auth. It is also known from U.S. Pat. No. 6,132,444 to Shturman (the instant inventor) et al., to provide a drive shaft with an abrasive element eccentrically positioned proximally to and spaced away from the distal end of the drive shaft.

Rotational angioplasty (atherectomy) is frequently used to remove atherosclerotic or other blocking material from stenotic (blocked) coronary arteries and other blood vessels. However, a disadvantage with this technique is that abraded particles can migrate along the blood vessel distally and block very small diameter vessels including capillaries of the heart muscle itself. The effect of the particulate debris produced by this procedure is of major concern to physicians who practice in this field. Clearly, the existence of particulate matter in the blood stream is undesirable and can cause potentially life-threatening complications, especially if the particles are over a certain size.

Although the potentially detrimental effect caused by the presence of abraded particles in the blood vessels is reduced if they are very small microparticles, it is much more preferable to remove from the treated blood vessel any debris abraded or otherwise released from the stenotic lesion during treatment and thereby prevent migration of debris to other locations along the treated blood vessel.

A rotational atherectomy device, described in U.S. Pat. No. 5,681,336 (to Clement et al.), has been proposed which attempts to prevent migration of abraded particles along the blood stream by removing the ablated material from the blood vessel whilst the device is in use. The rotational atherectomy device known from U.S. Pat. No. 5,681,336 (to Clement et al.) has a complicated construction and is difficult to manufacture on a commercial scale.

A number of disadvantages associated with the known rotational atherectomy devices have been addressed in WO 2006/126076 to Shturman (the instant inventor). The present invention seeks to further improve rotational atherectomy devices known from this document and other disadvantages associated with known atherectomy devices.

SUMMARY

According to the invention, there is provided a rotational atherectomy device for removing a stenotic tissue from a vessel of a patient, the device comprising a rotatable, flexible, hollow drive shaft having a distal end, the drive shaft comprising a fluid impermeable wall, an abrasive element mounted to the drive shaft proximal to and spaced away from its distal end, the fluid impermeable wall being formed from a torque transmitting coil and at least one fluid impermeable membrane which defines a lumen for the antegrade flow of pressurized fluid through the drive shaft and into a distal fluid inflatable support element to inflate said fluid inflatable support element, the distal fluid inflatable support element being located at the distal end of the drive shaft and having an outer wall comprising an outflow opening located such that said outflow opening faces an inner surface of a treated vessel during rotation of the drive shaft so that a flow of fluid out of said opening forms a layer of fluid between the outer wall of the fluid inflatable distal support element and a wall of the treated vessel, said layer of fluid forming a fluid bearing between the outer wall of the rotating fluid inflated distal support element and the wall of the treated vessel.

In one embodiment of the invention, the drive shaft has a longitudinal axis and the distal fluid inflatable support element has a centre of mass spaced radially away from the longitudinal axis of the drive shaft when the distal inflatable support element is fluid inflated.

Preferably, in this embodiment, a fluid inflatable space within the distal fluid inflatable support element extends only partially around a circumference of the drive shaft so that, when the distal inflatable support element is inflated with fluid its centre of mass is offset from a longitudinal axis of the drive shaft in one direction so that it acts as a counterweight to the abrasive element, which has its centre of mass offset from the longitudinal axis of the drive shaft in the opposite direction.

In another embodiment, the drive shaft has a longitudinal axis and the distal fluid inflatable support element has a centre of mass coaxial with the longitudinal axis of the drive shaft whenever the distal inflatable support element is fluid inflated. Preferably, in this embodiment, there are a plurality of openings in the outer wall of the fluid inflatable distal support element, said openings being located around the circumference of the outer wall of the fluid inflatable distal support element such that at any time during rotation of the drive shaft a flow of fluid through the opening forms a layer of fluid between the outer wall of the fluid inflatable distal support element and a wall of the treated vessel during rotation of said drive shaft, said layer of fluid forming a fluid bearing between the outer wall of the rotatable fluid inflated distal support element and the wall of the treated vessel.

In any embodiment of the invention, the fluid impermeable drive shaft may be provided with a proximal fluid inflatable support element located proximal to and spaced away from the abrasive element, the membrane that forms a fluid impermeable lumen for the antegrade flow of fluid along the torque transmitting coil into the distal fluid inflatable support element also forming a lumen for the antegrade flow of fluid along the torque transmitting coil into said proximal fluid inflatable support element to inflate said proximal fluid inflatable support element, wherein the proximal fluid inflatable support element has an outer wall formed by one of the fluid impermeable membranes, said outer wall of the proximal fluid inflatable support element having outflow openings located such that, at any time during rotation of the drive shaft and following inflation of the proximal fluid inflatable support element, at least one of said outflow openings is facing an inner surface of a treated vessel so that a flow of fluid through said opening(s) facing an inner surface of the treated vessel forms a layer of fluid between the outer wall of the fluid inflatable proximal support element and a wall of the treated vessel, said layer of fluid forming a fluid bearing between the outer wall of the rotating fluid inflatable proximal support element and the wall of the treated vessel.

In one embodiment the proximal fluid inflatable support element also preferably has a centre of mass spaced radially away from the longitudinal axis of the drive shaft when the proximal inflatable support element is fluid inflated which may be achieved by providing a fluid inflatable space within the proximal fluid inflatable support elements that extends circumferentially only partially around circumferential segments of the drive shaft. In this embodiment, when the proximal fluid inflatable support element is inflated with fluid its centre of mass becomes offset from a longitudinal axis of the drive shaft in one direction so it acts as a counterweight to the abrasive element, which has its centre of mass offset from the longitudinal axis of the drive shaft in the opposite direction.

In another embodiment, the drive shaft has a longitudinal axis and the proximal fluid inflatable support element has a centre of mass coaxial with the longitudinal axis of the drive shaft whenever the proximal inflatable support element is fluid inflated. In this embodiment there are a plurality of openings in the outer wall of the fluid inflatable proximal support element, said openings being located around the circumference of the outer wall of the fluid inflatable proximal support element such that at any time during rotation of the drive shaft a flow of fluid through the opening forms a layer of fluid between the outer wall of the fluid inflatable proximal support element and a wall of the treated vessel during rotation of said drive shaft, said layer of fluid forming a fluid bearing between the outer wall of the rotatable proximal fluid inflated support element and the wall of the treated vessel.

Preferably, in one embodiment, the fluid inflatable space within both the distal and proximal fluid inflatable support elements extends circumferentially only partially around circumferential segments which are spaced away in one direction with respect to the longitudinal axis of the drive shaft so that, when both the distal and proximal fluid inflatable support elements are inflated by fluid, their centers of mass become offset from a longitudinal axis of the drive shaft in said one direction and the distal and proximal fluid inflatable support elements act as counterweights to the abrasive element which is located on the drive shaft between the support elements and has its centre of mass offset from the longitudinal axis of the drive shaft in the opposite direction.

According to another preferred embodiment of the invention in which at least the distal inflatable support element has its centre of mass coaxial with the longitudinal axis of the drive shaft, the abrasive element also has its centre of mass coaxial with a longitudinal axis of the drive shaft. Whenever the centre of mass of the abrasive element is coaxial with a longitudinal axis of the drive shaft, preferably both the distal and proximal inflatable elements also have there centres of mass coaxial with the longitudinal axis of the drive shaft when inflated.

In preferred embodiments, a valve is formed near the distal end of the drive shaft. In the most preferred embodiment, said valve is a flexible leaf valve. The flexible leaf valve is preferably formed integrally with a wall of the distal fluid inflatable support element. The flexible leaf valve is moved to its closed position by pressure of fluid, which is pumped in an antegrade direction through the drive shaft after advancing the drive shaft over a guidewire across a stenotic lesion to be treated and withdrawing the guidewire from the drive shaft.

In one embodiment of the invention the abrasive element and both of the fluid inflatable support elements are symmetric with respect to the rotational (longitudinal) axis of the drive shaft. In another embodiment of the invention the abrasive element and the fluid inflatable support elements have their centres of mass spaced radially away from the rotational (longitudinal) axis of the drive shaft. In yet another embodiment of the invention the abrasive element has its centre of mass spaced away from the rotational (longitudinal) axis of the drive shaft while both of the distal and proximal fluid inflatable support elements have their centres of mass coaxial with the rotational (longitudinal) axis of the drive shaft.

The distal fluid inflatable support element preferably includes at least one inflow opening communicating a lumen of the fluid impermeable drive shaft with an interior space of the distal fluid inflatable support element, said space at least partially defined by a fluid impermeable membrane, the at least one inflow opening preferably having an axis which is perpendicular to a longitudinal axis of the fluid impermeable drive shaft.

In a preferred embodiment, the distal fluid inflatable support element includes at least one outflow opening communicating the interior space of the distal fluid inflatable support element with a vascular space within the vessel of the patient, at least one said outflow opening preferably having an axis which is about perpendicular to a longitudinal axis of the drive shaft when the distal inflatable support element is fluid inflated.

According to yet another aspect of the invention, there is provided a rotational atherectomy device, wherein the drive shaft is provided with a solid proximal support element located proximal to and spaced away from the abrasive element, the membrane that forms a fluid impermeable lumen for the antegrade flow of fluid through the drive shaft into the distal fluid inflatable support element also forming a lumen for the antegrade flow of fluid through the drive shaft into an outflow channel extending through said solid proximal support element, the solid proximal support element having a rounded outer surface, said outflow channel having an outflow opening in the rounded outer surface of the solid proximal support element such that, during rotation of the drive shaft, said outflow opening on the outer surface of the solid proximal support element is facing an inner surface of a treated vessel so that a flow of fluid out of said outflow opening forms a layer of fluid between the solid proximal support element and a wall of the treated vessel during rotation of the drive shaft, said layer of fluid forming a fluid bearing between the rotating solid proximal support element and the wall of the treated vessel.

According to another aspect of the invention, there is provided a rotational atherectomy device for removing a stenotic tissue from a vessel of a patient, the device comprising a turbine housing and a rotatable, flexible, hollow drive shaft having a distal end, a proximal end and, an abrasive element mounted to the drive shaft, the drive shaft comprising a torque transmitting coil and at least one fluid impermeable membrane forming an open-ended fluid impermeable lumen for the antegrade flow of fluid through the drive shaft from the proximal end of the drive shaft towards the distal end of the drive shaft, a proximal end portion of the drive shaft being attached to a distal end portion of a hollow turbine shaft rotatably mounted in the turbine housing, wherein a cylindrical stationary fluid supply tube comprising a distal end is received within the hollow turbine shaft to convey fluid from a pressurized fluid source into the proximal end of the drive shaft, the cylindrical wall of the stationary fluid supply tube having openings therein spaced from its distal end and facing the inner surface of the hollow, rotatable turbine shaft, the openings being configured such that a portion of the fluid flowing in an antegrade direction through the stationary fluid supply tube is re-directed through said openings to form a layer of fluid between the outer surface of the stationary fluid supply tube and the inner surface of the hollow rotatable turbine shaft, said layer of fluid acting as a fluid bearing between the stationary fluid supply tube and the rotatable turbine shaft.

In one embodiment, the openings in the cylindrical wall of the stationary fluid supply tube may extend in a radially outward direction relative to the axis of rotation of the hollow, rotatable turbine shaft.

The cylindrical stationary fluid supply tube is preferably received within the hollow rotatable turbine shaft such that fluid flowing in an antegrade direction out of the distal end of the stationary fluid supply tube traverses a portion of the hollow rotatable turbine shaft prior to flowing into the proximal end of the drive shaft.

According to another aspect of the invention, there is provided a turbine housing for a rotational atherectomy device for removing a stenotic tissue from a vessel of a patient, the turbine housing comprising a stationary cylindrical fluid supply tube received within a hollow rotatable turbine shaft, the cylindrical wall of the stationary fluid supply tube having openings therein spaced from its distal end and facing the inner surface of the hollow, rotatable turbine shaft, the openings being configured such that a portion of the fluid flowing in an antegrade direction through the stationary fluid supply tube is re-directed through said openings to form a layer of fluid between the outer surface of the stationary fluid supply tube and the inner surface of the hollow rotatable turbine shaft, said layer of fluid acting as a fluid bearing between the stationary fluid supply tube and the rotatable turbine shaft.

It should be appreciated that the present invention covers two most preferred embodiments. In a first most preferred embodiment, the fluid inflatable support elements are asymmetrical with respect to the longitudinal axis of the drive shaft and, in a second most preferred embodiment, the fluid inflatable support elements are symmetric with respect to the longitudinal axis of the drive shaft. However, it will be appreciated that, in all the embodiments, the asymmetric and symmetric fluid inflatable elements comprise outflow openings located such that, in the rotating drive shaft, fluid flowing through said openings forms fluid bearings between outer walls of said inflatable elements and the wall of the treated vessel.

It should be noted that throughout this specification, reference is made to "distal" and "proximal" ends and to flow of fluid in an "antegrade" and "retrograde" direction. For the avoidance of doubt, the distal end is considered to refer to the end of the device which is inserted into the vessel in the body of the patient and the proximal end is the end of the device which remains outside the body of the patient and which can be connected to a handle assembly for both rotating and longitudinally moving the drive shaft within the treated vessel. "Antegrade" flow refers to a direction of flow from the proximal towards the distal end of the device. Similarly, "retrograde" flow refers to a direction of flow in the opposite direction, i.e. from the distal towards the proximal end of the device.

BRIEF DESCRIPTION OF THE DRAWINGS

Embodiments of the invention will now be described, by way of example only, and with reference to the accompanying drawings, in which:

FIG. 4 illustrates the device of FIG. 3 located in a vessel being treated and showing how the device can be used in a curved vessel to abrade a stenotic lesion while forming fluid bearings between outer walls of symmetric fluid inflated support elements located distal and proximal to the abrasive element and the wall of the treated vessel;

FIG. 12 is an enlarged view of the distal end segment of the stationary fluid supply tube shown in FIG. 11.

DETAILED DESCRIPTION

In FIGS. 1 to 12, the direction of movement of the device is indicated by arrow marked "DM", the antegrade flow of fluid being indicated by arrows "FF" and the flow of fluid in a retrograde direction is indicated by arrows marked "R". Abraded particles AP abraded from the stenotic lesion 330 are aspirated into a lumen of a drive shaft sheath 5000 so that the retrograde flowing fluid and the abraded particles entrained in said fluid can be removed from the treated vessel and out of the patient's body.

Figure 1:
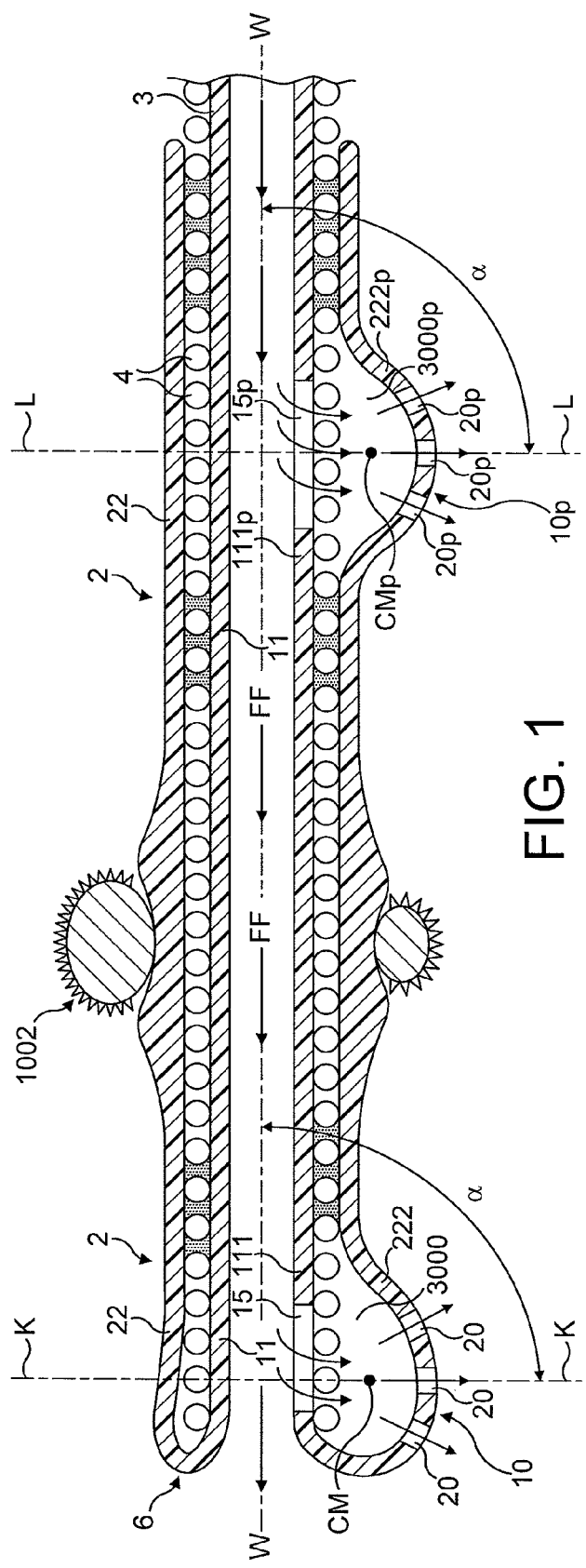
FIG. 1 illustrates in a longitudinal cross-section a distal portion of one preferred embodiment of the rotational atherectomy device of the invention, this embodiment comprising asymmetric fluid inflatable support elements and illustrates location of outflow openings in outer walls of said fluid inflatable support elements, the support elements being located distal and proximal to the abrasive element.

FIG. 1 illustrates in a longitudinal cross-section a distal portion of one preferred embodiment of the rotational atherectomy device of the invention. The rotational atherectomy device is comprised of an asymmetric abrasive element 1002 which extends around the entire circumference of the drive shaft 2 proximal to and spaced away from a distal end 6 of the drive shaft 2. The drive shaft 2 has a fluid impermeable membrane 3 which lines torque transmitting coil 4. Both the torque transmitting coil 4 and the fluid impermeable membrane 3 extend distally beyond the abrasive element 1002. The fluid impermeable membrane 3 is folded on itself at the distal end 6 of the drive shaft 2 and forms a distal fluid inflatable support element 10 between an inner 11 and outer 22 layers of the folded membrane 3. The outer layer 22 of the membrane 3 forms an outer wall 222 of the distal fluid inflatable support element 10 and the inner layer 11 of the membrane 3 forms an inner wall 111 of the distal fluid inflatable support element 10. The inner wall 111 of the distal fluid inflatable support element 10 has at least one inflow aperture (opening) 15 therein. The inflow aperture 15 of the distal fluid inflatable support element 10 communicates a fluid impermeable lumen of the drive shaft 2 with a fluid inflatable space 3000 of the distal fluid inflatable support element 10. FIG. 1 illustrates that a portion of flushing fluid FF flowing in an antegrade direction through the drive shaft 2 is redirected through the inflow aperture 15 into the distal fluid inflatable support element 10 to inflate said distal inflatable support element 10.

It should be noted that the inner and outer layers 11, 22 of the folded membrane may be formed by either folding the membrane 3 back onto itself or by inverting it.

FIG. 1 best illustrates that in order to form the distal fluid inflatable support element 10, the inner and outer layers 11, 22 of the folded fluid impermeable membrane 3 are connected or bonded to each other at least just proximal to the distal fluid inflatable support element 10. In this location, just proximal to the distal fluid inflatable support element 10, the inner and outer layers 11, 22 of the membrane 3 are preferably connected or bonded to each other around the entire circumference of the drive shaft 2.

In the most preferred embodiment of the invention the outer wall 222 of the distal fluid inflatable support element 10 has at least one outflow opening 20 which enables flow of fluid out of the distended fluid inflatable distal support element 10. The distal fluid inflatable support element 10 becomes distended by flow of fluid through the inflow aperture 15 in its inner wall 111. The inflow aperture 15 communicates a fluid impermeable lumen of the drive shaft 2 with an inflatable space 3000 within the distal fluid inflatable support element 10, said inflatable space 3000 is at least partially defined by a fluid impermeable membrane which forms the outer wall 222 of the distal fluid inflatable support element 10.

An area of the inflow aperture 15 through which fluid enters the distal inflatable support element 10 is larger than the area of the outflow opening(s) 20 through which fluid exits the distal fluid inflatable support element 10 so that the distal fluid inflatable support element 10 is kept inflated by the pressure of fluid flowing through the distal fluid inflatable support element 10.

FIG. 1 shows the distal fluid inflatable support element 10 in its inflated state. FIG. 1 illustrates that the distal fluid inflatable support element 10 is asymmetric with respect to a longitudinal axis W-W of the drive shaft 2. After being inflated by fluid, such asymmetric distal support element has its centre of mass CM spaced away from the longitudinal axis W-W of the drive shaft 2. FIG. 1 shows an abrasive element 1002 which is mounted to the drive shaft 2 proximal to and spaced away from the asymmetric distal fluid inflatable support element 10. The abrasive element 1002 extends around the entire circumference of the drive shaft 2 and has its centre of mass spaced radially away from the longitudinal axis W-W of the drive shaft. Preferably, the centre of mass CM of the asymmetric fluid inflated distal support element 10 is spaced radially away from the longitudinal axis W-W of the drive shaft in one direction and the centre of mass of the abrasive element 1002 is spaced radially away from the longitudinal axis W-W of the drive shaft in another diametrically opposite direction, so that in a rotating drive shaft such asymmetric fluid inflated distal support element 10 becomes a distal fluid inflatable counterweight with respect to the abrasive element 1002.

FIG. 1 illustrates that the outer wall 222 of the fluid inflated distal support element 10 is bowing longitudinally outwards at least along its longitudinally middle section which extends in a longitudinal cross-section between an outflow opening 20 which is located longitudinally most distally within the outer wall 222 and another outflow opening 20 which is located longitudinally most proximally within the outer wall 222.

Each outflow opening 20 in the outer wall 222 of the distal fluid inflatable support element has its own axis K-K. FIG. 1 illustrates that the asymmetric distal fluid inflatable support element 10 when inflated has at least one outflow opening 20 in its longitudinally rounded outer wall 222 located such that the axis K-K of the outflow opening 20 forms an acute angle of at least sixty (60) degrees with respect to the longitudinal axis W-W of the drive shaft 2. In the most preferred embodiment of the invention, the asymmetric distal fluid inflatable support element 10 when inflated has at least one outflow opening 20 in its outer wall 222 located such that the axis K-K of the outflow opening 20 forms an angle α of about ninety (90) degrees with respect to the longitudinal axis W-W of the drive shaft.

Figure 2:
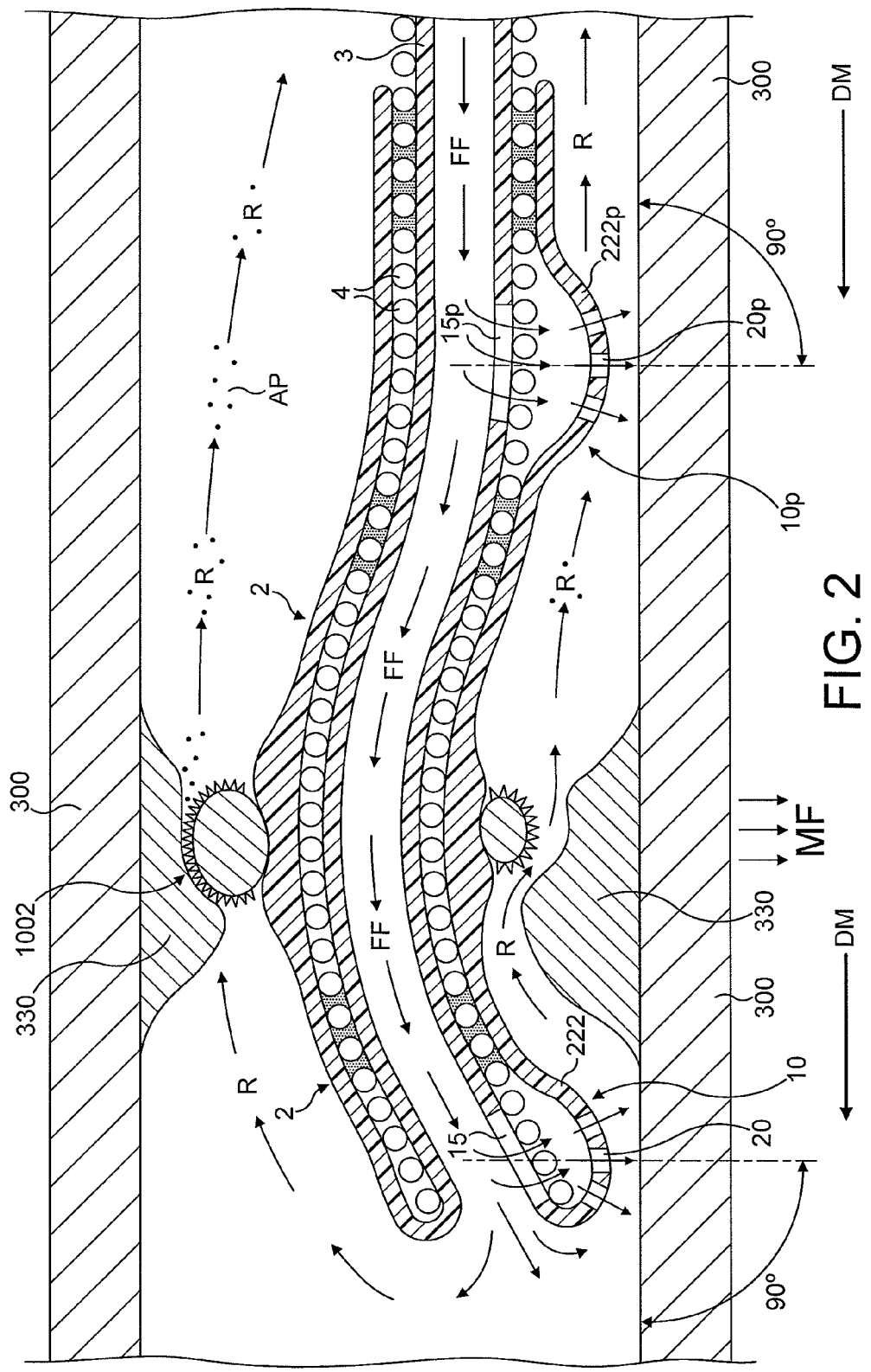
FIG. 2 illustrates the device of FIG. 1 located in a vessel being treated and showing how the device can be used to abrade a stenotic lesion while forming fluid bearings between outer walls of the asymmetric fluid inflated support elements and the wall of the treated vessel.

FIG. 2 illustrates that in the rotating asymmetric fluid inflated distal support element 10 at least one of the above described outflow openings 20 is located such that its axis forms about a ninety (90) degrees angle with respect to the inner surface of the wall 300 of the treated vessel. Centrifugal force attempts to press a rotating asymmetric fluid inflated distal support element 10 against the wall 300 of the treated vessel, but fluid exiting from the outflow opening 20 along its axis at an angle of about ninety (90) degrees with respect to the wall 300 of the vessel forms a thin layer of fluid between the outer wall 222 of the fluid inflated distal support element 10 and an inner surface of the wall 300 of the vessel. Preferably, the fluid inflated distal support element 10 with the centre of mass radially spaced away from the longitudinal (rotational) axis of the drive shaft should have at least one outflow opening 20 in the outer wall 222 of the distal inflatable support element 10 located such that at any time during rotation of the drive shaft 2 said outflow opening 20 is facing an inner surface of the treated vessel so that a flow of fluid through the opening 20 forms a layer of fluid between the outer wall 222 of the rotating fluid inflated distal support element 10 and the wall of a treated vessel. Said layer of fluid forms a fluid bearing between the outer wall 222 of the rotating fluid inflated distal support element 10 and the wall of the treated vessel.

It should be noted that in the most preferred embodiments of the invention, the fluid impermeable drive shaft is provided with two fluid inflatable support elements, one located at the distal end of the drive shaft and the other proximal to and spaced away from the abrasive element. FIG. 1 illustrates one such embodiment in which the drive shaft 2 is provided with both a distal fluid inflatable support element 10 and a proximal fluid inflatable support element 10p. The proximal fluid inflatable support element 10p has an inner wall 111p and an outer wall 222p. In the most preferred embodiment of the invention, the outer wall 222p of the proximal fluid inflatable support element 10p is formed by the outer layer 22 of the folded fluid impermeable membrane 3. The inner wall 111p of the proximal fluid inflatable support element 10p is formed by the inner layer 11 of the folded fluid impermeable membrane 3. The inner wall 111p of the proximal fluid inflatable support element 10p has an inflow aperture 15p therein. FIG. 1 illustrates that a portion of flushing fluid FF flowing in an antegrade direction through the drive shaft 2 is redirected through the inflow aperture 15p into the proximal fluid inflatable support element 10p to inflate said proximal fluid inflatable support element. FIG. 1 illustrates best that in order to form the proximal fluid inflatable support element 10p, the inner 11 and outer 22 layers of the folded fluid impermeable membrane 3 are connected or bonded to each other at least just distal and proximal to the proximal fluid inflatable support element 10p. In this location, just distal and proximal to the proximal fluid inflatable support element 10p, the inner 11 and the outer 22 layers of the membrane 3 are preferably connected or bonded to each other around the entire circumference of the drive shaft 2.

It should be noted that the outer wall of the proximal fluid inflatable support element may be formed not only by a proximal portion of the outer layer 22 of the folded fluid impermeable membrane 3, but by a separate fluid impermeable membrane connected or bonded circumferentially to the fluid impermeable membrane 3 at least just distal and proximal to the proximal fluid inflatable support element.

The following discussion is focused on the design and function of the proximal fluid inflatable support element 10p which has its outer wall 222p formed by the outer layer 22 of the folded fluid impermeable membrane 3, but it should be understood that the same discussion would be applicable to a proximal fluid inflatable support element which has its outer wall formed by the separate fluid impermeable membrane. The following discussion is particularly applicable with respect to the location and function of openings in the outer wall of the proximal fluid inflatable support element.

In the most preferred embodiment of the invention the outer wall 222p of the proximal fluid inflatable support element 10p has at least one outflow opening 20p which enables flow of fluid out of the distended fluid inflatable proximal support element 10p. The proximal fluid inflatable support element 10p becomes distended by flow of fluid through its inflow aperture 15p which communicates the lumen of the fluid impermeable drive shaft 2 with the inflatable space 3000p within the proximal fluid inflatable support element 10p. The fluid inflatable space 3000p is at least partially defined by a fluid impermeable membrane which forms an outer wall 222p of the proximal fluid inflatable support element 10p.

An area of the inflow aperture 15p through which fluid enters the proximal fluid inflatable support element 10p is larger than the area of the outflow opening(s) 20p through which fluid exits the proximal fluid inflatable support element 10p so that the proximal fluid inflatable support element 10p is kept inflated by the pressure of the fluid flowing through the proximal fluid inflatable support element 10p.

FIG. 1 shows the proximal fluid inflatable support element 10p in its inflated state. FIG. 1 illustrates that the proximal fluid inflatable support element 10p is asymmetric with respect to a longitudinal axis of the drive shaft. After being inflated by fluid, such asymmetric proximal support element 10p has its centre of mass CMp spaced away from the longitudinal axis W-W of the drive shaft 2. FIG. 1 shows an abrasive element 1002 which is mounted to the drive shaft 2 distal to and spaced away from the asymmetric proximal fluid inflatable support element 10p. The asymmetric abrasive element 1002 extends around the entire circumference of the drive shaft 2 and has its centre of mass spaced radially away from the longitudinal axis W-W of the drive shaft 2. Preferably, the centre of mass CMp of the asymmetric fluid inflated proximal support element 10p is spaced radially away from the longitudinal axis W-W of the drive shaft in one direction and the centre of mass of the asymmetric abrasive element 1002 is spaced radially away from the longitudinal axis W-W of the drive shaft 2 in another diametrically opposite direction, so that in a rotating drive shaft such asymmetric fluid inflated proximal support element 10p becomes a proximal fluid inflatable counterweight with respect to the abrasive element 1002.

FIG. 1 illustrates that the outer wall 222p of the fluid inflated proximal support element 10p is bowing longitudinally outwards at least along its longitudinally middle section which extends in a longitudinal cross-section between an outflow opening 20p which is located longitudinally most distally within the outer wall 222p and another outflow opening 20p which is located longitudinally most proximally within the outer wall 222p.

Each outflow opening 20p in the outer wall 222p of the proximal fluid inflatable support element has its own axis L-L. FIG. 1 illustrates that the asymmetric proximal fluid inflatable support element 10p when inflated has at least one outflow opening 20p in its outer wall 222p located such that the axis L-L of the outflow opening 20p forms an acute angle of at least sixty (60) degrees with respect to the longitudinal axis W-W of the drive shaft 2. In the most preferred embodiment of the invention, the asymmetric proximal fluid inflatable support element 10p when inflated has at least one outflow opening 20p in its outer wall 222p located such that the axis L-L of the outflow opening 20p forms about a ninety (90) degrees angle α with respect to the longitudinal axis W-W of the drive shaft 2. FIG. 2 illustrates that in the rotating asymmetric fluid inflated proximal support element 10p at least one of the above described outflow openings 20p is located such that its axis forms about a ninety (90) degrees angle with respect to the inner surface of the wall 300 of the treated vessel. Centrifugal force attempts to press a rotating asymmetric fluid inflated proximal support element 10p against the wall 300 of the treated vessel, but fluid exiting from the outflow opening 20p along its axis at an angle of about ninety (90) degrees with respect to the wall 300 of the vessel forms a thin layer of fluid between the rounded outer wall 222p of the fluid inflated proximal support element 10p and an inner surface of the wall 300 of the vessel.

FIG. 2 illustrates rotation of the fluid inflated proximal support element 10p with the centre of mass radially spaced away from the longitudinal (rotational) axis of the drive shaft. Centrifugal force attempts to press the rotating fluid inflated proximal support element 10p against the wall 300 of the vessel, but at least one outflow opening 20p in the longitudinally rounded outer wall 222p of the rotating fluid inflated proximal support element 10p is located such that a flow of fluid through said opening 222p forms a layer of fluid between the outer wall 222p of the rotating fluid inflated proximal support element 10p and the wall 300 of the treated vessel. Preferably, the fluid inflated proximal support element 10p with the centre of mass radially spaced away from the longitudinal (rotational) axis of the drive shaft 2 should have at least one outflow opening 20p in the longitudinally rounded outer wall 222p of the proximal inflatable support element 10p located such that at any time during rotation of the drive shaft 2 said outflow opening 20p is facing an inner surface of the treated vessel so that a flow of fluid through the outflow opening 20p forms a layer of fluid between the longitudinally rounded outer wall 222p of the rotating fluid inflated proximal support element 10p and the wall 300 of a treated vessel. Said layer of fluid forms a fluid bearing between the outer wall 222p of the rotating fluid inflated proximal support element 10p and the wall 300 of the treated vessel.

Figure 3:
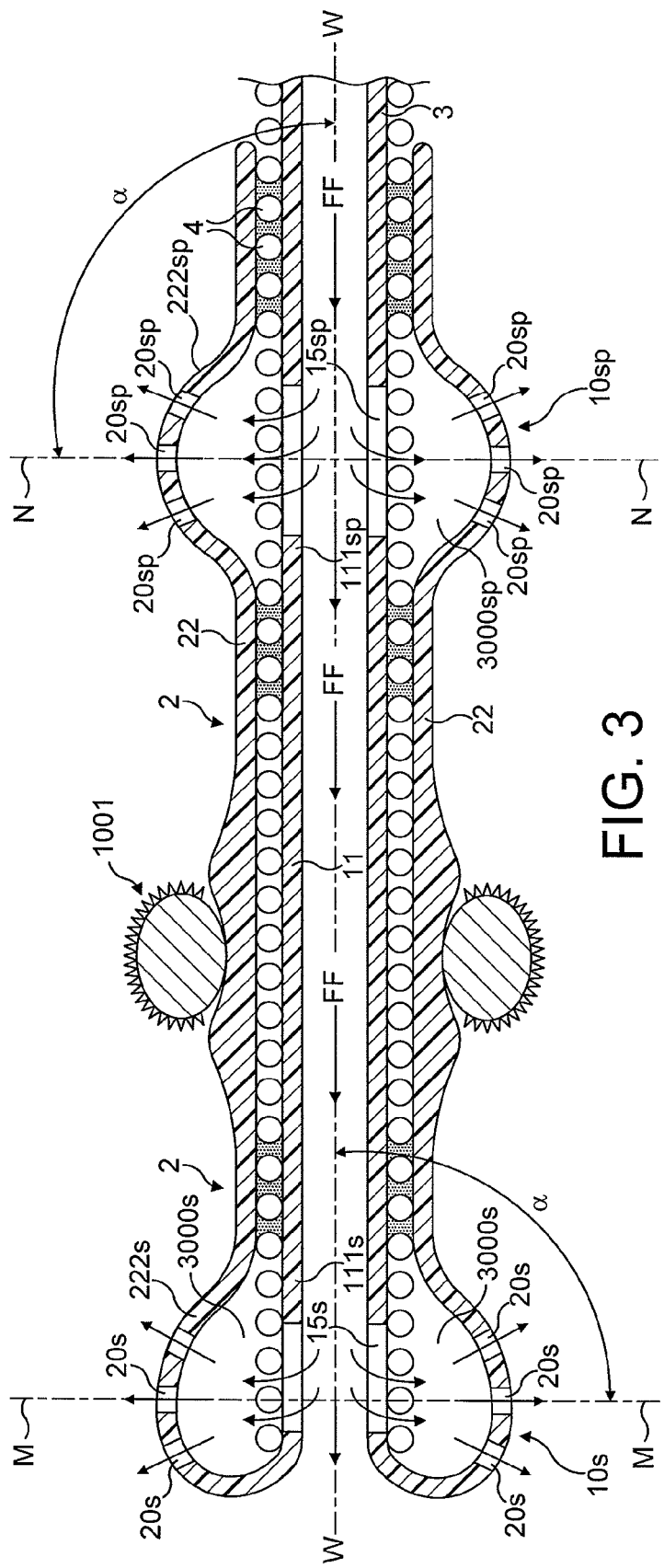
FIG. 3 illustrates in a longitudinal cross-section a distal portion of another preferred embodiment of the rotational atherectomy device of the invention, this embodiment comprising symmetric fluid inflatable support elements and illustrates location of outflow openings in outer walls of said fluid inflatable support elements, the support elements being located distal and proximal to the abrasive element.

FIG. 3 illustrates another preferred embodiment of the distal end portion of the rotational atherectomy device of the invention. In this embodiment both the abrasive element 1001 and the distal fluid inflatable support element 10s are symmetric with respect to a longitudinal axis W-W of the drive shaft. The symmetric abrasive element 1001 extends around the entire circumference of the drive shaft 2 and is located proximal to and spaced away from the symmetric distal fluid inflatable support element 10s. The symmetric distal fluid inflatable support element 10s has a fluid inflatable space 3000s which extends uniformly around the drive shaft 2, so that after being inflated by fluid the distal support element 10s has its centre of mass coaxial with the longitudinal axis W-W of the drive shaft 2. An inflow aperture 15s communicates the fluid inflatable space 3000s within the fluid inflatable support element 10s with the lumen of the fluid impermeable drive shaft 2. The fluid inflatable space 3000s is defined by a fluid impermeable membrane which forms at least a portion of the wall 222s of the symmetric distal fluid inflatable support element 10s.

FIG. 3 illustrates in a longitudinal cross-section that the symmetric fluid inflatable support element has a maximum diameter circumference when inflated and that the outer wall 222s of the fluid inflated symmetric distal support element 10s is bowing longitudinally outward at least along the maximum diameter circumference of the fluid inflated symmetric distal support element. The outer wall 222s of the symmetric distal fluid inflatable support element 10s has at least one outflow opening 20s. Preferably, the symmetric distal fluid inflatable support element 10s has at least two outflow openings 20s in its outer wall 222s. Each outflow opening 20s in the outer wall 222s of the symmetric distal fluid inflatable support element 10s has its own axis M-M. The Figure illustrates that the symmetric distal fluid inflatable support element 10s, when inflated, has at least one outflow opening 20s in its outer wall 222s located such that the axis M-M of the outflow opening 20s forms an acute angle of at least sixty (60) degrees with respect to the longitudinal axis W-W of the drive shaft 2. In the most preferred embodiment of the invention, the symmetric distal fluid inflatable support element 10s when inflated has at least one outflow opening 20s in its outer wall 222s located such that the axis M-M of the outflow opening 20s forms about a ninety (90) degrees angle α with respect to the longitudinal axis W-W of the drive shaft.

Figure 5:
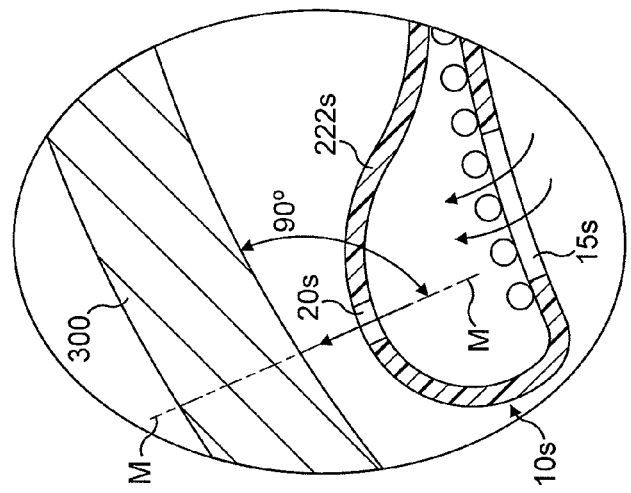

FIGS. 4 and 5 illustrate that in the rotating symmetric fluid inflated distal support element 10s at least one of the above described outflow openings 20s is located such that its axis M-M forms about a ninety (90) degrees angle with respect to the inner surface of the wall 300 of the treated vessel. FIGS. 4 and 5 also illustrate that in a curved vessel the drive shaft 2 attempts to maintain its straight configuration and therefore attempts to press a rotating symmetric distal fluid inflated support element 10s against the outer curvature of the vessel but fluid exiting from the outflow opening 20s along its axis M-M at an angle of about ninety (90) degrees with respect to the wall 300 of the vessel forms a thin layer of fluid between the outer wall 222s of the fluid inflated distal support element 10s and the inner surface of the outer curvature of the wall 300 of the treated vessel.

Preferably, the fluid inflated symmetric distal support element 10s should have at least few outflow openings 20s located around the circumference of the outer wall 222s, the outflow openings 20s located in a longitudinally bowing outward segment of the outer wall 222s such that at any time during rotation of the drive shaft 2 at least one of these outflow openings 20s is facing an inner surface of the treated vessel so that a flow of fluid through the outflow opening 20s forms a layer of fluid between the outer wall 222s of the rotating fluid inflated symmetric distal support element 10s and the wall 300 of the treated vessel. Said layer of fluid forms a fluid bearing between the outer wall 222s of the rotating fluid inflated distal support element 10s and the wall 300 of the treated vessel.

It should be noted that in the most preferred embodiments of the invention, the fluid impermeable drive shaft is provided with two symmetric fluid inflatable support elements, one located at the distal end of the drive shaft and the other proximal to and spaced away from the abrasive element 1001. FIG. 3 illustrates one such embodiment in which the drive shaft 2 is provided with both a symmetric distal fluid inflatable support element 10s and a symmetric proximal fluid inflatable support element 10sp. The symmetric proximal fluid inflatable support element 10sp has an inner wall 111sp and an outer wall 222sp. In the most preferred embodiment of the invention, the outer wall 222sp of the symmetric proximal fluid inflatable support element 10sp is formed by the outer layer 22 of the folded fluid impermeable membrane 3. The inner wall 111sp of the symmetric proximal fluid inflatable support element 10sp is formed by the inner layer 11 of the folded fluid impermeable membrane 3. The inner wall 111sp of the symmetric proximal fluid inflatable support element 10sp has an inflow aperture 15sp therein. This inflow aperture 15sp communicates the lumen of the fluid impermeable drive shaft 2 with an inflatable space 3000sp within the symmetric proximal fluid inflatable support element 10sp. The inflatable space 3000sp is at least partially defined by a fluid impermeable membrane which forms the outer wall 222sp of the symmetric proximal fluid inflatable support element 10sp. FIG. 3 illustrates that a portion of flushing fluid FF flowing in an antegrade direction through the drive shaft 2 is redirected through the inflow aperture 15sp into the symmetric proximal fluid inflatable support element 10sp to inflate said symmetric proximal fluid inflatable support element. FIG. 3 illustrates best that in order to form the symmetric proximal fluid inflatable support element 10sp, the inner 11 and outer 22 layers of the folded fluid impermeable membrane 3 are connected or bonded to each other at least just distal and proximal to the symmetric proximal fluid inflatable support element 10*sp*. In this location, just distal and proximal to the symmetric proximal fluid inflatable support element 10*sp*, the inner 11 and the outer 22 layers of the membrane 3 are preferably connected or bonded to each other around the entire circumference of the drive shaft 2.

It should be noted that the outer wall 222*sp* of the symmetric proximal fluid inflatable support element 10*sp* may be formed not only by a proximal portion of the outer layer 22 of the folded fluid impermeable membrane 3, but by another fluid impermeable membrane.

Figure 7:
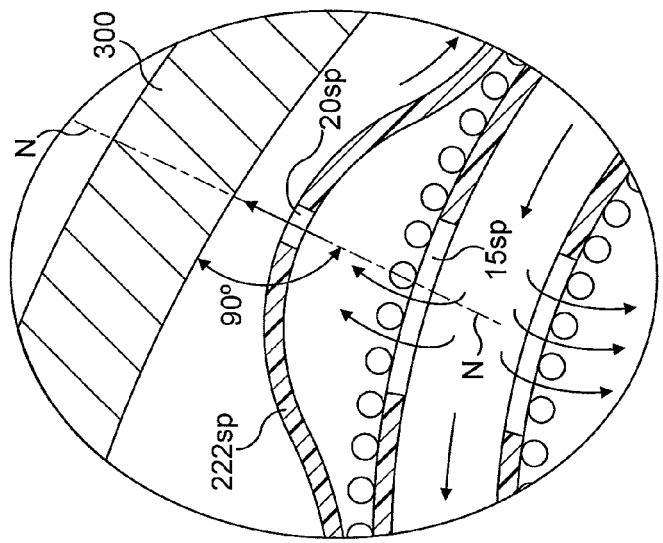
FIGS. 5 to 7 are enlarged views of portions of the atherectomy device shown in FIG. 4.
Figure 6:
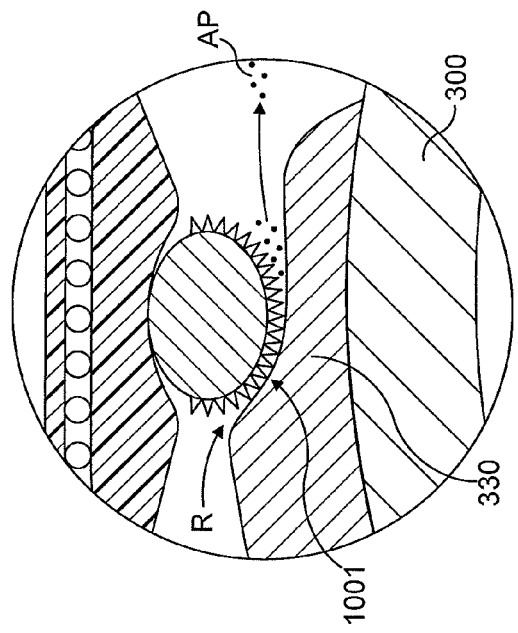

The outer wall 222*sp* of the symmetric proximal fluid inflatable support element 10*sp* has at least one outflow opening 20*sp*. Preferably, the symmetric proximal fluid inflatable support element 10*sp* has at least two outflow openings 20*sp* in its outer wall 222*sp*. Each outflow opening 20*sp* in the outer wall 222*sp* of the symmetric proximal fluid inflatable support element 10*sp* has its own axis N-N. FIG. 3 illustrates that the symmetric proximal fluid inflatable support element 10*sp* when inflated has at least one outflow opening 20*sp* in its outer wall 222*sp* located such that the axis N-N of the outflow opening 20*sp* forms an acute angle of at least sixty (60) degrees with respect to the longitudinal axis W-W of the drive shaft. In the most preferred embodiment of the invention, the symmetric proximal fluid inflatable support element 10*sp* when inflated has at least one outflow opening 20*sp* in its outer wall 222*sp* located such that the axis N-N of the outflow opening 20*sp* forms about a ninety (90) degrees angle α with respect to the longitudinal axis W-W of the drive shaft 2. FIGS. 4 and 7 illustrate that in the rotating symmetric fluid inflated proximal support element 10*sp* at least one of the above described outflow openings 20*sp* is located such that its axis N-N forms about a ninety (90) degrees angle with respect to the inner surface of the wall 300 of the treated vessel. FIGS. 4 and 7 also illustrate that in a curved vessel the drive shaft 2 attempts to maintain its straight configuration and therefore attempts to press a rotating symmetric proximal fluid inflated support element 10*sp* against the outer curvature of the vessel but fluid exiting from the outflow opening 20*sp* along its axis N-N at an angle of about ninety (90) degrees with respect to the wall 300 of the vessel forms a thin layer of fluid between the outer wall 222*sp* of the fluid inflated proximal support element 10*sp* and an inner surface of the wall 300 of the vessel.

Preferably, the fluid inflated symmetric proximal support element 10*sp* should have at least few outflow openings 20*sp* spaced about equally around the circumference of the outer wall 222*sp*, the openings located such that at any time during rotation of the drive shaft 2 at least one of these outflow openings 20*sp* is facing an inner surface of the treated vessel so that a flow of fluid through the outflow opening 20*sp* forms a layer of fluid between the outer wall 222*sp* of the rotating fluid inflated symmetric proximal support element 10*sp* and the wall 300 of the treated vessel. Said layer of fluid forms a fluid bearing between the outer wall 222*sp* of the rotating fluid inflated proximal support element 10*sp* and the wall 300 of the treated vessel.

FIG. 4 illustrates that in a curved vessel the drive shaft 2 attempts to maintain its straight configuration and therefore attempts to press a rotating abrasive element 1001 towards the inner curvature of a curved vessel. As known from WO 2006/126076 this allows preferential removal of stenotic lesion 330 located along the inner curvature of the treated vessel. It is also known from WO 2006/126076 that magnetic forces MF, shown in FIG. 4, may be used to bias abrasive element in any desirable direction with respect to the circumference of the treated vessels.

It should be noted that the rotational atherectomy device comprising symmetrical fluid inflatable support elements may also be used successfully in a straight vessel where said elements, when supported by fluid bearings, allow safe rotation of the drive shaft within the treated vessel even after the guidewire has been removed from the rotational atherectomy device. The rotational atherectomy device with symmetric fluid inflatable support elements preferably comprises either an eccentric abrasive element with a centre of mass spaced away from the longitudinal axis of the drive shaft or, an abrasive element which is capable of being magnetically biased in any direction with respect to the circumference of the treated vessel.

Figure 8:
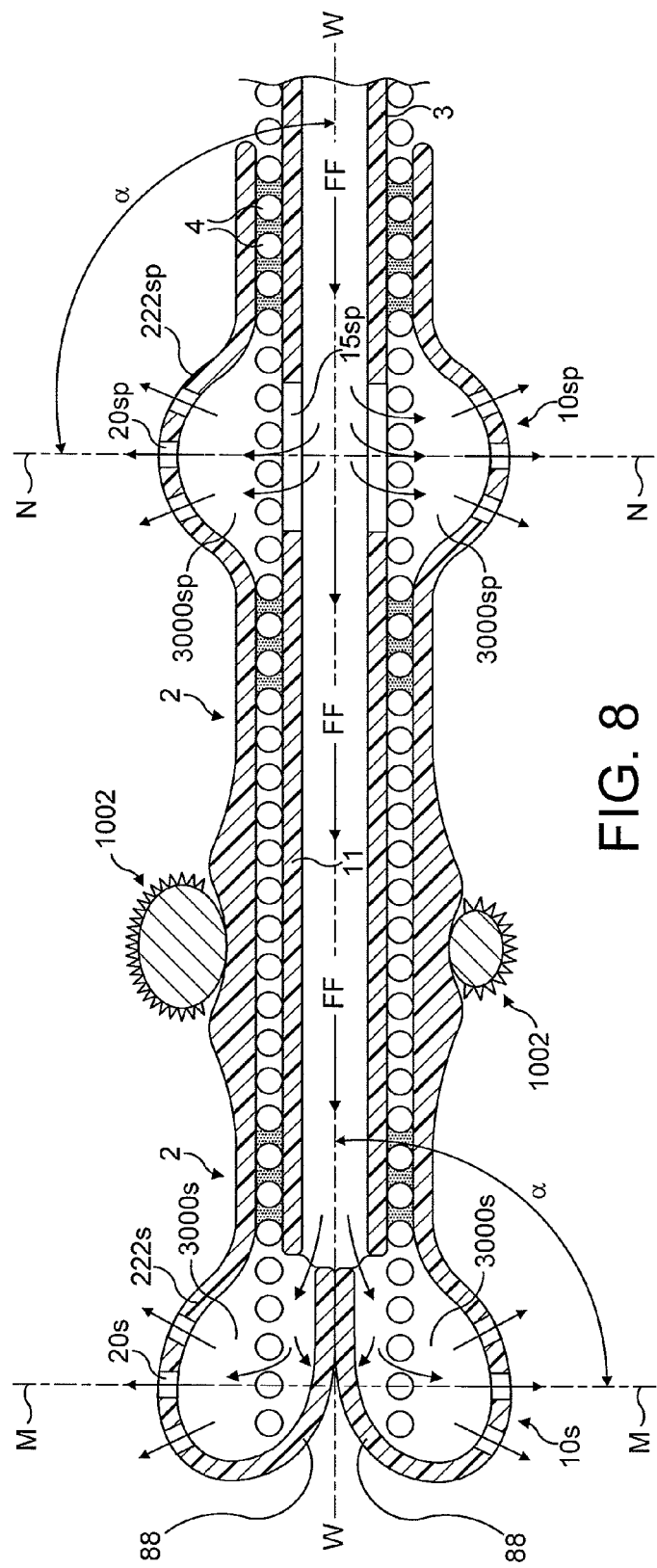
FIG. 8 is generally similar to FIG. 3 but shows the formation of a flexible leaf valve, said valve having one or more leaflets.

FIG. 8 illustrates a fluid impermeable drive shaft with two symmetric fluid inflatable support elements and an asymmetric abrasive element 1002 mounted on the drive shaft between said symmetric fluid inflatable support elements. FIG. 8 also shows at least one valve 88 located at the distal end of the lumen of the fluid impermeable drive shaft 2. This valve 88 may be comprised of one or more flexible leaflets and is shown in its closed position, thereby preventing flow of flushing fluid through the distal end of the drive shaft and assisting in directing the flushing fluid into the distal symmetric fluid inflatable support element.

Figure 9:
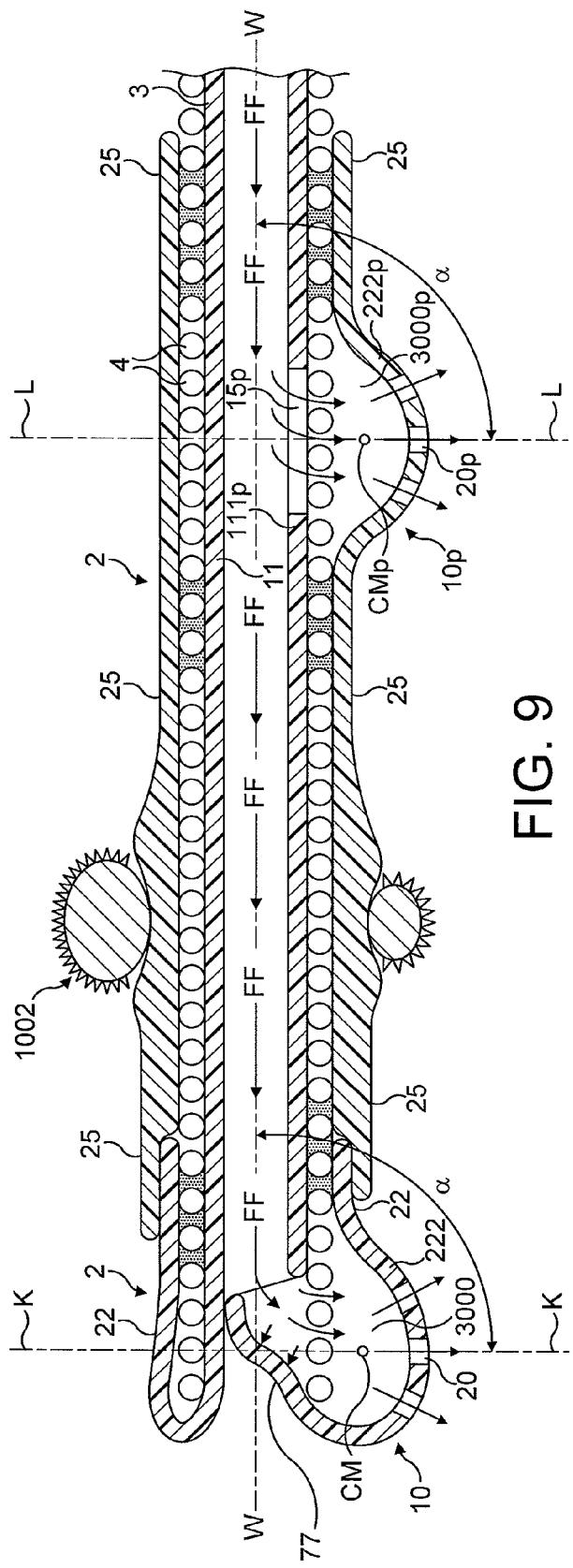
FIG. 9 is generally similar to FIG. 1 but shows the formation of a flexible leaf valve, said valve having one or more leaflets.

FIG. 9 illustrates that a valve 77 which is similar to valve 88 may be formed at the distal end of a lumen of the drive shaft with the asymmetric fluid inflatable support elements 10 and 10*p*. The valve 77 may be comprised of one or more leaflets. FIG. 9 also illustrates that a separate membrane 25 may extend around the drive shaft 2 proximal to the distal fluid inflatable support element 10. Preferably, the separate membrane 25 is fluid impermeable so that it can form an outer wall 222*p* of the proximal fluid inflatable support element 10*p*. If the distal fluid inflatable element 10 is formed from a stretchable membrane 3 then the membrane 25 should be made from a non-stretchable material.

Figure 10:
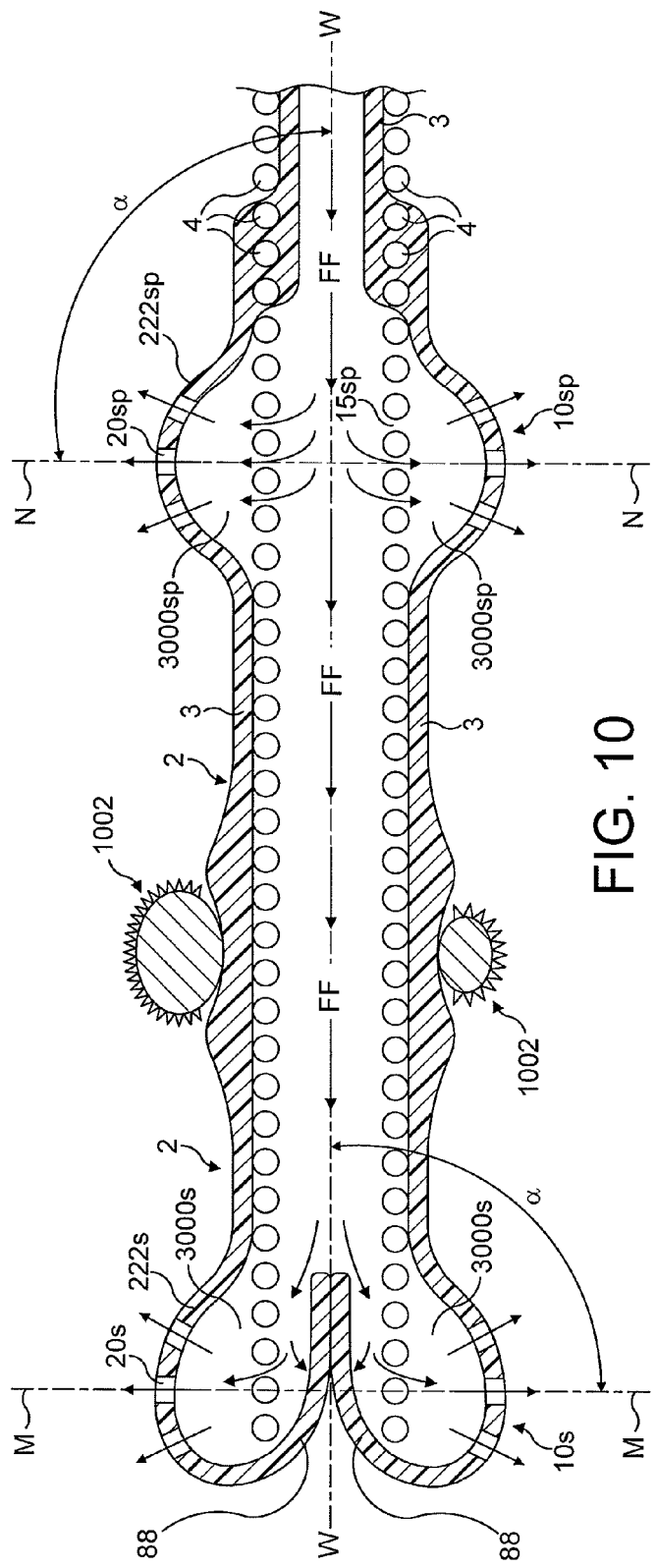
FIG. 10 is generally similar to FIG. 8 but shows a rotational atherectomy device with symmetric fluid inflatable support elements which are formed integrally with a fluid impermeable membrane by using manufacturing methods of injection molding, insertion molding or other currently available progressive manufacturing methods.

FIG. 10 shows a rotational atherectomy device with symmetric fluid inflatable support elements which are formed integrally with a fluid impermeable membrane 3 without folding the membrane on itself at the distal end of the drive shaft but instead making said inflatable support elements integral with the membrane 3 by using manufacturing methods of injection molding, insertion molding or other currently available progressive manufacturing methods. It should be understood that similar progressive manufacturing methods may be used in producing a rotational atherectomy device with asymmetric fluid inflatable support elements.

Figure 10A:
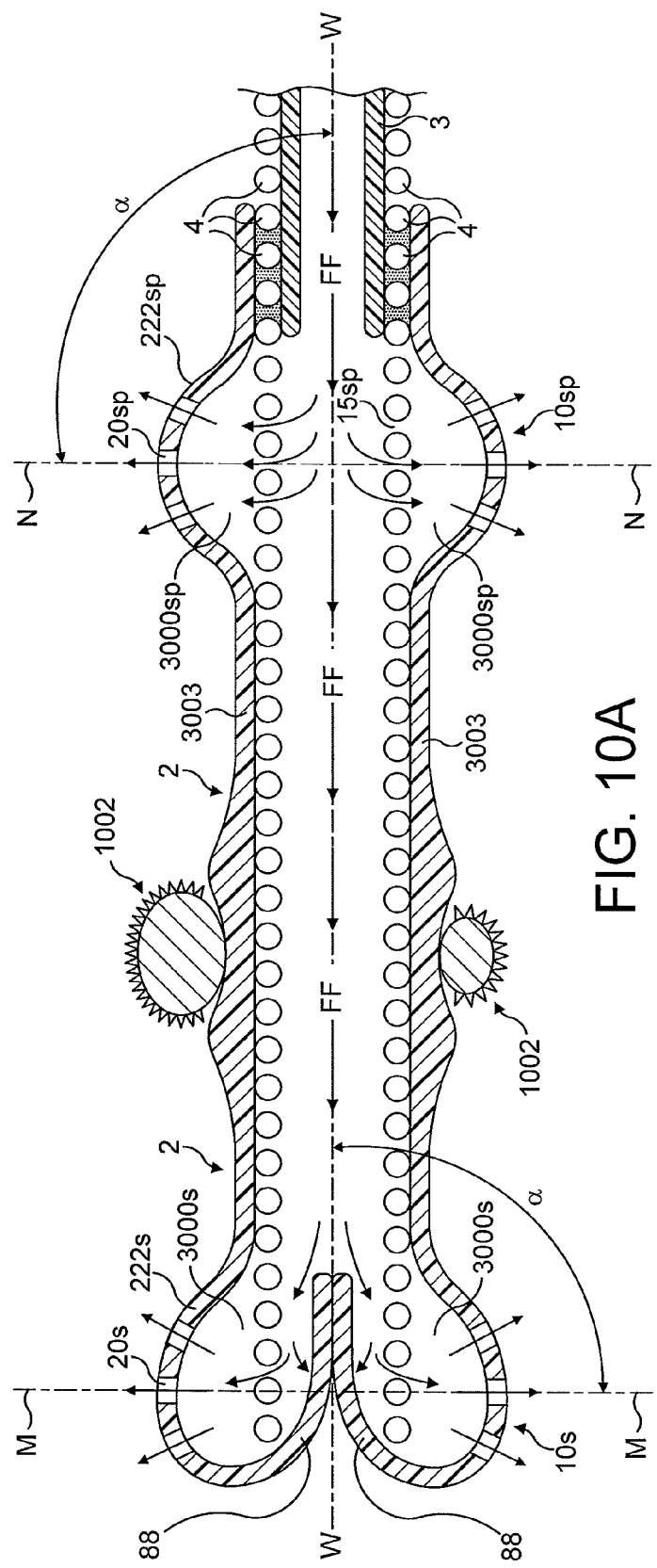
FIG. 10A illustrates an embodiment in which the distal end portion of the atherectomy device which incorporates the fluid inflatable elements is injection moulded so that the membrane extending over the torque transmitting coil is separate to the membrane which may line or may extend around the torque transmitting coil proximal to the distal end portion of the device.

FIG. 10A illustrates an embodiment in which the distal end portion of the atherectomy device, which incorporates the fluid inflatable elements, is injection moulded so that the membrane 3003 extending over the torque transmitting coil along the distal end portion of the device is separate to the membrane which may line or may extend over the torque transmitting coil proximal to the distal end portion of the device.

FIG. 2 illustrates that an orbit of the asymmetric abrasive element may be biased, in any direction with respect to the circumference of the treated vessel, by an external magnetic force illustrated by arrows MF. FIG. 4 illustrates that the position of the symmetric abrasive element 1001 with respect to the circumference of the vessel also may be affected by an external magnetic force illustrated by arrows MF. It should be understood that the external magnetic force may be utilized to move in the desired direction any of the abrasive elements described above and shown in FIGS. 1 through 9.

Figure 11:
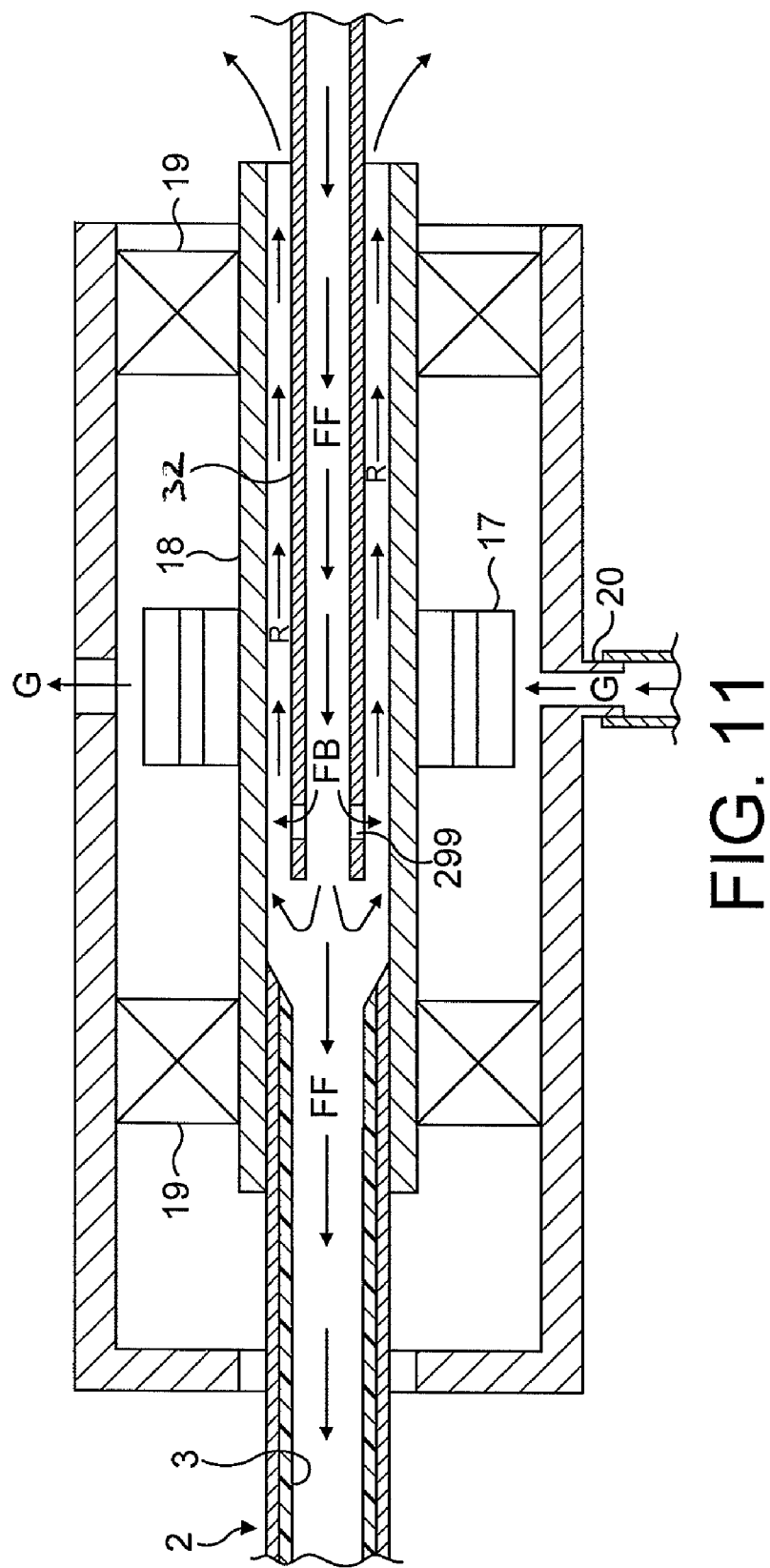
FIG. 11 illustrates a cross-sectional view through a turbine housing of the rotational atherectomy device according to the present invention, and shows how a fluid beating is formed between a distal end segment of a stationary fluid supply tube and a rotatable turbine shaft by providing radially outward directed openings in the wall of the stationary fluid supply tube.

FIGS. 11 and 12 illustrate that a wall of the stationary fluid supply tube 32 preferably should have at least three openings located near its distal end and equally spaced around the circumference of the fluid supply tube 32. FIGS. 11 and 12 illustrate an embodiment with at least four such openings 299. FIG. 12 illustrates that each opening 299 has an axis P-P which is perpendicular to a longitudinal (rotational) axis W-W of the fluid supply tube 32. FIG. 11 illustrates that a flow of fluid through openings 299 forms a fluid bearing between the stationary fluid supply tube 32 and the rotatable turbine shaft 18. The turbine shaft 18 is connected to a flexible, hollow, fluid impermeable drive shaft 2. It should be noted that the most proximal portion of the fluid impermeable drive shaft 2 is shown in FIG. 11.

Many modifications and variations of the invention falling within the terms of the following claims will be apparent to a person skilled in the art and the foregoing description should be regarded as a description of the preferred embodiments only.

The invention claimed is:

1. A rotational atherectomy device for removing a stenotic lesion from a vessel of a patient, the device comprising an abrasive element mounted to a distal end portion of a rotatable, flexible, hollow drive shaft proximal to and spaced away from a fluid inflatable distal support element fixedly positioned at a distal end of the drive shaft such that the fluid inflatable distal support element rotates together with the abrasive element in response to rotation of the drive shaft, wherein the abrasive element comprises a solid body that extends around an entire circumference of the drive shaft and comprises an abrasive outer surface that is fixedly positioned relative to the drive shaft, the drive shaft having a longitudinal axis and a fluid impermeable wall which extends along a length of the drive shaft to a region of the distal end portion of the drive shaft having one or more apertures and defines a fluid impermeable guide wire lumen of the drive shaft, the fluid impermeable guide wire lumen being configured for advancement of the drive shaft over a guidewire across the stenotic lesion and for transfer of pressurized fluid into a fluid inflatable space of the distal support element after crossing the stenotic lesion and removing the guidewire from the drive shaft or withdrawing it into the drive shaft, the distal support element being inflatable by pressurized fluid which flows into a proximal end portion of the fluid impermeable guide wire lumen, flows in an antegrade direction through the lumen and is at least partially re-directed into the distal fluid inflatable support element, the proximal end portion of the fluid impermeable guide wire lumen being located outside of a body of the patient, the distal fluid inflatable support element having an outer wall comprising an outflow opening located such that said outflow opening faces an inner surface of a vessel during rotation of the drive shaft, the outflow opening having an axis which forms an angle of at least about seventy five (75) degrees with the longitudinal axis of the drive shaft when the distal fluid inflatable support element is inflated, so that the outflow opening is configured to output fluid flow during rotation of the fluid inflated distal support element for forming a layer of fluid between the outer wall of the rotating fluid inflated distal support element and a wall of the vessel, said layer of fluid being operable to form a fluid bearing between the outer wall of the rotating fluid inflated distal support element and the wall of the vessel during rotation and back and forth movements of the drive shaft within the vessel after removing the guidewire from the drive shaft or withdrawing it into the drive shaft.

2. A rotational atherectomy device according to claim 1, wherein the drive shaft is comprised of a torque transmitting coil and at least one fluid impermeable membrane.

3. A rotational atherectomy device according to claim 2, wherein the fluid inflatable space within the distal fluid inflatable support element extends only partially around a circumference of the drive shaft so that, when the distal inflatable support element is inflated with fluid, its center of mass is offset from the longitudinal axis of the drive shaft in one direction while a center of mass of the abrasive element is offset from the longitudinal axis of the drive shaft in the opposite direction.

4. A rotational atherectomy device according to claim 1, wherein the distal fluid inflatable support element has a center of mass which coincides with the longitudinal axis of the drive shaft when the distal support element is fluid inflated, the distal fluid inflatable support element having a plurality of outflow openings in its outer wall, said openings being located around a maximum circumference of the outer wall of the fluid inflatable distal support element, the outflow openings having axes which form angles of about ninety (90) degrees with the longitudinal axis of the drive shaft when the distal support element is fluid inflated.

5. A rotational atherectomy device according to claim 3, wherein the drive shaft is provided with a proximal fluid inflatable support element which has a fluid inflatable space and is located proximal to and spaced away from the abrasive element, wherein both the proximal and distal fluid inflatable distal support elements rotate together with the abrasive element in response to rotation of the drive shaft, both the distal and proximal fluid inflatable support elements having fluid inflatable spaces that extend circumferentially only partially around a circumference of the drive shaft so that, when both the distal and proximal fluid inflatable support elements are inflated by fluid, their centers of mass become offset from a longitudinal axis of the drive shaft in one direction while a center of mass of the abrasive element located between the support elements is offset from the longitudinal axis of the drive shaft in the opposite direction.

6. A rotational atherectomy device according to claim 4, wherein the abrasive element has its center of mass spaced radially away from the longitudinal axis of the drive shaft.

7. A rotational atherectomy device according to claim 4, wherein the center of mass of the abrasive element coincides with the longitudinal axis of the drive shaft.

8. A rotational atherectomy device according to claim 5, wherein the proximal support element is inflatable by pressurized fluid which flows in the antegrade direction through the fluid impermeable lumen of the drive shaft and is re-directed into the proximal fluid inflatable support element, the proximal fluid inflatable support element having an outer wall which comprises an outflow opening located such that an axis of the outflow opening forms an angle of at least about seventy five (75) degrees with the longitudinal axis of the drive shaft when the proximal fluid inflatable support element is inflated, said outflow opening is configured to output fluid flow during rotation of the fluid inflated proximal support element for forming a layer of fluid between the outer wall of the rotating fluid inflated proximal support element and the wall of the vessel, said layer of fluid being operable to form a fluid bearing between the outer wall of the rotating fluid inflated proximal support element and the wall of the treated vessel.

9. A rotational atherectomy device according to claim 1, wherein the drive shaft is provided with a valve, said valve being located at the distal end of the drive shaft and configured to occlude the fluid impermeable guide wire lumen at its distal end and thereby prevent flow of fluid through the very distal end of the guide wire lumen and assist in re-directing flow of fluid into the distal fluid inflatable support element.

10. A rotational atherectomy device according to claim 9, wherein the valve is a flexible leaf valve, the flexible leaf valve configured to be moved to its closed position by pressure of fluid which is pumped in the antegrade direction through the drive shaft after advancing the drive shaft over the guidewire across a stenotic lesion to be treated and removing the guide wire from the drive shaft or withdrawing it into the drive shaft.

11. A rotational atherectomy device for removing a stenotic tissue from a vessel of a patient, the device comprising a turbine housing and a rotatable, flexible, hollow drive shaft having a distal end, a proximal end, a fluid-inflatable distal support element mounted to the distal end of the drive shaft, and an abrasive element mounted to the drive shaft at a position that is proximal to and spaced away from the fluid-inflatable distal support element such that the abrasive element rotates together with the fluid-inflatable distal support element in response to rotation of the drive shaft, wherein the abrasive element comprises a solid body mounted on the drive shaft and an abrasive outer surface that is fixedly positioned relative to the drive shaft, the drive shaft comprising a torque transmitting coil and at least one fluid impermeable membrane forming a fluid impermeable lumen for an antegrade flow of fluid through the drive shaft from the proximal end of the drive shaft towards the fluid inflatable distal support element at the distal end of the drive shaft, wherein a proximal end portion of the drive shaft is attached to a distal end portion of a hollow turbine shaft rotatably mounted in the turbine housing and, a cylindrical stationary fluid supply tube is received within the hollow turbine shaft to provide a flow of pressurized fluid from a fluid source into the fluid impermeable lumen of the drive shaft, the cylindrical wall of the stationary fluid supply tube comprising a plurality of openings which extend in a radially outward direction relative to an axis of rotation of the rotatable turbine shaft, the openings facing an inner surface of the rotatable turbine shaft, said openings in the cylindrical wall of the stationary fluid supply tube configured such that a portion of the pressurized fluid flowing in the antegrade direction through the stationary fluid supply tube is re-directed through the openings to form a layer of fluid between the outer surface of the stationary fluid supply tube and the inner surface of the hollow rotatable turbine shaft, said layer of fluid forming a fluid bearing between the stationary fluid supply tube and the rotatable turbine shaft.

12. A rotational atherectomy device according to claim 11, wherein the cylindrical stationary fluid supply tube is received within the hollow rotatable turbine shaft such that pressurized fluid flowing in the antegrade direction out of the distal end of the stationary fluid supply tube traverses a portion of the hollow rotatable turbine shaft prior to flowing into the fluid impermeable lumen of the drive shaft.

13. A rotational atherectomy device according to claim 4, wherein the drive shaft is provided with a proximal fluid inflatable support element located proximal to and spaced away from the abrasive element, wherein both the proximal and distal fluid inflatable distal support elements rotate together with the abrasive element in response to rotation of the drive shaft, both the distal and proximal support elements being inflatable by pressurized fluid which flows in the antegrade direction through the fluid impermeable guide wire lumen and is re-directed into the inflatable support elements, both the distal and proximal support elements having fluid inflatable spaces that extend around an entire circumference of the drive shaft and are defined by outer walls of the support elements, the outer walls of the inflatable support elements comprising multiple outflow openings, said openings being located around a maximum circumference of the outer wall of each of the fluid inflatable support elements such that, during rotation of the drive shaft, said openings are configured to output fluid flow for forming layers of fluid between the outer walls of the fluid inflated support elements and the wall of the vessel, said layers of fluid being operable to form fluid bearings between the outer walls of the rotating fluid inflated support elements and the wall of the vessel during rotation and back and forth movements of the drive shaft within the vessel after removing the guidewire from the drive shaft or withdrawing it into the drive shaft.

14. A rotational atherectomy device according to claim 13, wherein the abrasive element has its center of mass spaced radially away from the longitudinal axis of the drive shaft.

15. A rotational atherectomy device according to claim 13, wherein the center of mass of the abrasive element coincides with the longitudinal axis of the drive shaft.

16. A rotational atherectomy device for removing a stenotic lesion from a vessel of a patient, the device comprising an abrasive element mounted to a distal end portion of a rotatable, flexible, hollow drive shaft between a distal fluid-inflatable support element being located at a distal end of the drive shaft and a proximal fluid-inflatable support element located on the drive shaft, wherein the abrasive element comprises a solid body that extends around an entire circumference of the drive shaft and comprises an abrasive outer surface that is fixedly positioned relative to the drive shaft, wherein both the distal and proximal fluid-inflatable support elements rotate together with the abrasive element in response to rotation of the drive shaft, each of the distal and proximal fluid-inflatable support elements having a fluid inflatable space which is in fluid communication with a distal end portion of a guide wire lumen of the drive shaft, the guide wire lumen having a proximal end portion located outside of the patient and a fluid impermeable wall which extends along a length of the guide wire lumen to a region of the distal end portion of the guide wire lumen in fluid communication with the distal and proximal fluid-inflatable support elements, the distal and proximal fluid-inflatable support elements being inflatable by pressurized fluid which flows into the proximal end portion of the fluid impermeable guide wire lumen, flows in an antegrade direction through said lumen and is at least partially re-directed into the distal and promixal fluid-inflatable support element, the fluid impermeable guide wire lumen being configured for advancement of the drive shaft over a guidewire across the stenotic lesion to be treated and for transfer of pressurized fluid into the fluid inflatable space of each of the distal and proximal fluid-inflatable support elements after removing the guidewire from the drive shaft or withdrawing it into the drive shaft, the drive shaft having a longitudinal axis and the abrasive element and each of the support elements having their individual centers of mass, the center of mass of the abrasive element being spaced radially away from the longitudinal axis of the drive shaft while the center of mass of the distal support fluid-inflatable element and the center of mass of the proximal fluid-inflatable support element each coincide with the longitudinal axis of the drive shaft.

* * * * *